United States Patent [19]

Casley-Smith

[11] Patent Number: 4,593,041

[45] Date of Patent: Jun. 3, 1986

[54] BENZO-PYRONES AS A TREATMENT FOR SCHIZOPHRENIA

[76] Inventor: John R. Casley-Smith, 97 Seaview Rd., Tennyson, South Australia, Australia

[21] Appl. No.: 711,647

[22] Filed: Mar. 14, 1985

[51] Int. Cl.$^4$ .............................................. A61K 31/35
[52] U.S. Cl. .................................................... 514/457
[58] Field of Search ......................................... 514/457

[56] References Cited

PUBLICATIONS

Merck Index, 7th Ed. (1976), pp. 1255 & 333.

Primary Examiner—Stanley J. Friedman
Attorney, Agent, or Firm—Oldham, Oldham & Weber Co.

[57] ABSTRACT

The invention relates to the treatment of schizophrenia and senile macular degeneration by administering any one of the benzo-pyrone group of drugs.

4 Claims, No Drawings

BENZO-PYRONES AS A TREATMENT FOR SCHIZOPHRENIA

This invention relates to the treatment of schizophrenia, and also to the treatment of senile diffuse macular degeneration.

BACKGROUND OF THE INVENTION

Some workers consider that some forms of schizophrenia are associated with high-protein oedema, leading to excess fibrosis in the brain. Hence there follows a general discussion of oedema and the use of benzo-pyrones in the treatment of high-protein oedema.

Oedema is an abnormal accumulation of fluid in the tissue spaces or cavities of the body. There are five main factors in the formation of generalised oedema and a sixth which plays an important role in the formation of local oedema. They are:

1. Permability of the capillary wall,
2. & 3. Colliodal osmotic pressure of the plasma proteins in the blood and tissues.
4. & 5. Hydro-static pressures in the capillaries and tissues and
6. Lymphatic obstruction.

Thus oedema is an unusual swelling of the tissue due to an excessive amount of fluid and can be the result of various causes. Thus haematoma, or in other words a bruise, is one of the most common oedemas. The causes of oedema fall naturally into four groups corresponding to the four classes of oedema, thus 1. High-flow low-protein,
2. High-flow high-protein,
3. Low-flow high protein, as well as a fourth group of causes of oedema "safety valve insufficiency" which occurs when lymphostasis is superimposed on what would normally be a high flow oedema produced either by excess blood vascular leakage, or the obstruction of a duct of an organ (kidney, pancreas, etc.) the results of which are particularly disastrous for the tissues.

High-Protein oedemas are very common in all communities. It has been found that one person in three seeks medical attention every year, in South Australia, for a condition associated with one. The W.H.O. estimates that 250,000,000 people suffer from lymphoedema and elephantiasis, while 250,000 women in Australia suffer from lymphoedema of the arm, of varying grades of severity, after mastectomy. It is highly probably that the improvement produced by the benzo-pyrone group of drugs, in so many different diseases, is because they have high-protein oedema associated with them. This always causes reduced oxygenation and function of the tissues. If the oedema is reduced, oxygenation and function are improved. While these drugs do not affect the basic diseases, the reduction they produce in associated oedemas improve the function of the tissues and thus the normal healing processes proceed more expeditiously. Examples of this are: lymphoedema, accidential and surgical trauma, haematomas, pancreatitis, hepatitis and cirrhosis.

BRIEF STATEMENT OF THE INVENTION

It has been found that the group of benzo-pyrones are highly beneficial in the treatment of oedemas, particularly high-protein oedemas.

Thus there is provided according to the invention that the benzo-pyrone group of drugs are used as a treatment for schizophrenia; or exudative or disciform maculopathy.

DESCRIPTION OF THE PREFERRED EMBODIMENT

It has been shown that these drugs can effectively reduce high-protein oedemas and they do this by increasing the normal proteolysis of the tissues and (to some extent) by increasing lymphatic function. They are thus effective in all diseases which have high-protein oedema as part of their disorders. While they do not cure any underlying disease, the fact that they reduce the associated high-protein oedema means that they relieve much pain and loss of function. In addition all oedemas cause lowered oxygenation and much harm to the tissues. The high-protein ones in particular (if prolonged) cause chronic inflammation and thus their removal is of considerable benefit.

The benzo-pyrones are a group of compounds which include a number of sub-groups. They contain the flavonoids and their derivatives, coumarin and its derivatives and a variety of other groups.

It has been found that the benzo-pyrones as noted above are very effective in the treatment of high-protein oedemas. It has been found that the use of the benzo-pyrone affects the oedema in four ways 1. Excessive protein loss from the blood vessels can be reduced,
2. Protein and fluid removal by the lymphatics can (under certain conddditions) be increased,
3. More phagocytosis of protein by cells in the tissues occurs, and
4. The intracellular or extracellular, lysis of proteins by cells in the tissues are made greater.

It should be realised however that it may be rare for a benzo-pyrone to have only one action in a particular disease; similarly, it is rare for a particular disease to have only one cause or to derange only one of the body's functions. Thus for example a burn gives a high protein oedema because of the injured blood vessels, but frequently the collecting lymphatics go into spasm producing a superimposed lymphoedema, i.e. there is a 'safety-valve' insufficiency; treating a burn with a benzo-pyrone may well affect the open blood capillary endothelial junctions, interfere with the mediators of inflammation, alter the permeability of the interstitial tissue, increase the extravascular proteolysis and cause the collecting lymphatics to pump more lymph.

Benzo-pyrones while often opening blood vascular junctions, can greatly reduce blood vascular endothelial damage in certain circumstances. These include preventing the opening of the post capillary venular endothelial junctions, preventing endothelial cells leaving the vessel wall with a consequent huge gap in its lining, and acting as vitamin-P substances when the patient is deficient in this.

It has been shown that benzo-pyrones can increase the pumping capacity of the collecting lymphatics and that they also cause an increased production of urine.

Increased phagocytosis may indeed occur, but the phagocytosed macromolecules are not retained in the tissues. In burns the removal of the protein was considerably increased by coumarin under all conditions. The removal of a non-metabolisable tracer PVP, was slowed by the coumarin in the normal and burnt legs-possibly because phagocytosis was enhanced (with the non-metabolisable PVP being retained in the phagocytes); the PVP was however more rapidly removed with coumarin in the presence of lymphodema—probably because the reduction of oedema reduced the distances it had to travel to reach blood capillaries. The important thing is that the protein removal from the limbs was much more rapid with coumarin. This shows that it is not simply phagocytosed and retained in the phagocytes in the region.

It has also been shown by exclusion that, when the benzo-pyrones reduce high-protein oedemas they must increase proteolysis and secondly it was found that the ratios of radio-labelled-protein-fragments, to the labelled protein, increased greatly when treated with coumarin, thirdly that the benzo-pyrones have been shown to induce increased levels of proteases in the oedema fluid, in the whole tissues, and in the plasma and lymph and fourthly they increase proteolysis by macrophags in vitro, fifthly they lose their ability to reduce high-protein oedemas when the macrophags are selectively poisoned.

Thus it can be seen that the use of benzo-pyrones, particularly coumarin is particularly effective in reducing all forms of oedema, and the dosage and treatment will vary according to the particular oedema being treated.

Schizophrenia is a term which probably includes a number of different diseases, of differing aetiology. While they have broad clinical similarities, they differ in course, in severity and in what forms of treatment are most effective.

At least two of the benzo-pyrones (coumarin and troxerutin) have been shown to be effective in considerably improving a large proportion of patients with both acute and chronic schizophrenia. Since one is an alpha-benzo-pyrone and the other a gamma, it appears that the whole group has this property. This is particularly likely since it has been shown that quite diverse members of this group have very similar properties, differing only in degree. (It is unknown whether the sub-group of benzo-pyrones which have anti-coagulant properties could be given in large enough amounts to have this effect; however there are so many benzo-pyrones with no, or minimal, anticoagulant activity that it is considered unnecessary even to contemplate the use of those with this property.)

It is unknown why schizophrenia should respond to these compounds. Possible explanations are:
1. Some workers consider that some forms of schizophrenia are associated with high-protein oedema, leading to excess fibrosis, in the brain, as discussed above. This group of drugs will reduce both the oedema and its consequent fibrosis.
2. Some workers consider that schizophrenia is caused by an imbalance in prostaglandin production. The benzo-pyrones are known to reduce the one which is considered to be in excess.
3. Megadoses of some of the B group of vitamins are considered, by some workers, to reduce schizophrenia in many patients. It has been shown that the benzo-pyrones can replace $B_6$ and $B_3$ in certain conditions. Since large doses of the benzo-pyrones have been used in the treatment of schizophrenia, it may be that they are acting in the manner of megaB-vitamin therapy.
4. A few workers consider that schizophrenia can be caused by a lack of adrenalin. The benzo-pyrones are known to reduce its catabolism.

It has been found that a daily dose of 2 tablets each containing 200 mg couramin is effective in the treatment of schizophrenia, as are 12 capsules of O-($\beta$-hydroxyethyl)-rutosides (troxerutin)- each containing 250 mg.

Also it is considered by some workers that exudative or disciform maculopathy is caused by high-protein oedemas, and hence the use of benzo-pyrones can be effective in the treatment of this disease also. Thus these drugs can be effectively used in the treatment of any high-protein oedemas occurring in the head, the retina and brain being closely associated in the head.

While reference is made throughout the specification to the treatment of the diseases, it is to be realised that it is not intended that a complete cure is achieved in every case, and that normality may not be completely restored, but that the drugs are effective in the treatment or relief of the disease.

I claim:
1. A method of treating high protein oedema, schizophrenia or disciform maculopathy in humans by daily administering orally to a human in need of such treatment from about 400 to about 3000 mg of a drug from the group consisting of courmarin and troxerutin.
2. A method as defined in claim 1 characterised in that 400 mg of the drug coumarin is administered by tablet form daily.
3. A method as defined in claim 1 characterised in that 3 g of the drug troxerutin [O-($\beta$-hydroxyethyl)-rutosides] is administered daily.
4. A method as defined in claim 1 characterized in that the drug is administered orally.

* * * * *